United States Patent

Takasaki et al.

[11] Patent Number: 5,124,262
[45] Date of Patent: Jun. 23, 1992

[54] MANNOSE ISOMERASE AND PROCESS FOR MANNOSE PRODUCTION USING IT

[75] Inventors: Yoshiyuki Takasaki, Miyazaki; Takaichi Ohya, Aichi, both of Japan

[73] Assignee: Amano Pharmaceutical Co., Ltd., Nagoya, Japan

[21] Appl. No.: 661,139

[22] Filed: Feb. 27, 1991

[30] Foreign Application Priority Data

Feb. 28, 1990 [JP] Japan ................................. 2-48908

[51] Int. Cl.$^5$ ........................... C12N 9/90; C12P 19/24
[52] U.S. Cl. ...................................... 435/233; 435/94; 435/105; 435/183
[58] Field of Search ........................... 435/94, 233, 105

[56] References Cited

U.S. PATENT DOCUMENTS 4,069,104 1/1978 Barker et al. ...................... 435/94
4,492,755 1/1985 Horwath et al. .................. 435/233

OTHER PUBLICATIONS

"Agricultural and Biological Chemistry," (1964) vol. 28, pp. 601–604.
"Agricultural and Biological Chemistry," (1964) vol. 28, pp. 605–609.
"Annual of Agency of Industrial Science & Technology," (1965) vol. 28, pp. 89–94.
"Journal of Biological Chemistry," (1956) vol. 218, pp. 535–548.
Pallerini et al., J. Biol. Chem., vol. 218, p. 535 (1956).

Primary Examiner—Ronald W. Griffin
Assistant Examiner—Pamela S. Webber
Attorney, Agent, or Firm—Wegner, Cantor, Mueller & Player

[57] ABSTRACT

A mannose isomerase having excellent properties for industrial use, such as high thermal stability and resistance to high substrate concentrations, can be produced by culturing a strain of Pseudomonas (sp. AM-9582), and extracting it from the cells of AM-9582. Mannose can be effectively produced from fructose of high concentrations using the enzyme.

2 Claims, 3 Drawing Sheets

MANNOSE ISOMERASE AND PROCESS FOR MANNOSE PRODUCTION USING IT

BACKGROUND OF THE INVENTION

1. Field of the Invention

This invention relates to a novel mannose isomerase which catalyses the mutual conversion reaction between D-mannose (hereinafter referred as mannose) and D-fructose (hereinafter referred as fructose), a process for producing it and a process for producing mannose from fructose using it.

2. Related Background Art

It has been recently shown that mannose inhibits the growth of harmful enterobacteria Salmonella [R. H. Brown, Foodstuff, Jun. 12, 10 (1989)], indicating its utilization as feed additives for fowls such as chickens, or as bioactive food materials. However, mannose is very expensive because it is ordinarily prepared by hydrolysing mannan contained in vegetables such as woods or konjak (devil's tongue).

The present inventors have been seeking after microorganisms being capable of producing industrially usable mannose isomerase which converts fructose to mannose reversibly, in order to establish a technique to produce mannose from fructose which is produced abundantly and inexpensively, as well as a technique for preparing mannose directly from glucose with the combination use of mannose isomerase and glucose isomerase which converts glucose to fructose reversibly. Consequently, a bacterium was isolated which has been identified as one strain of the genus Pseudomonas producing a mannose isomerase markedly excellent in thermal stability as compared with those known in the prior art.

Mannose isomerase was found by Palleroni and Doudoroff et al in 1956 as the first enzyme of the isomerizing enzymes for free hexoses in *Pseudomonas saccharophila* [J. Biol. Chem., Vol. 218, p. 535 (1956)]. Later, the present inventors found that a bacterial strain isolated from soil and identified as *Xanthomonas ruburilineans* produced a mannose isomerase [Journal of Agricultural Chemical Society of Japan, Vol. 37, P. 524–528 (1963), Agric. Biol. Chem., Vol. 28, p. 601–604 (1964)], and also presence of a similar enzyme in *Streptomyces aerocolorigenes* [Annual Report of Fermentation Institute, Agency of Industrial Science & Technology. Vol. 28. p. 89–94 (1966)]. However, all of these enzymes have optimum temperatures at 35° to 40° C. and are poor in thermal stability, and therefore cannot be utilized in industry.

SUMMARY OF THE INVENTION

The object of the present invention is to provide:

1. A mannose isomerase having the following physicochemical properties:
   (a) enzyme action: isomerizing mannose to fructose and vice versa;
   (b) substrate specificity: active on D-mannose and D-lyxose, but substantially not on D-rhamnose, D-fucose, D-glucose, D-ribose, D-xylose, D-arabinose, L-xylose, L-arabinose, L-rhamnose, L-fucose;
   (c) optimum pH: around pH 8 at 50° C.
   (d) optimum temperature: around 55° C. at pH 7.0 for 30 minutes;
   (e) thermal stability: up to around 55° C., at pH 7.0 for 10 minutes;
   (f) pH stability: around pH 6 to 9 at 25° C., for 3 hours
   (g) inhibition: enzyme activity being inhibited by mercury ions, iron ions, silver ions, aluminum ions and p-chloromercury benzoate.

2. A process for preparing a mannose isomerase, which comprises culturing biologically pure culture of a micoorganism from the genus Pseudomonas, the microorganism being capable of producing the mannose isomerase according to claim 1, allowing the culture to produce the mannose isomerase and collecting the enzyme.

3. A process for preparing mannose which comprises allowing a mannose isomerase of claim 1 to act in a fructose containing-liquid and collecting the mannose containing liquid thus obtained.

4. A process for producing mannose which comprises:
   (a) immobilizing the microorganisms being capable of producing mannose isomerase of claim 1 onto a carrier; and
   (b) circulating a fructose solution through the immobilized cells; and
   (c) collecting the mannose containing liquid thus obtained.

5. A biological pure culture of Pseudomonas sp. AM9582 (FERM-BP-3207), being capable of producing a thermostable mannose isomerase stable at 55° C. for 10 minutes, having physiological properties of arginine dihydrolase positive, phenylalanine deaminase negative, starch decomposition negative, levan production negative and acylamidase positive.

DETAILED DESCRIPTION OF THE INVENTION

Seeking after the previously mentioned purpose the present inventors have found that a microorganism isolated from soil and identified to belong to the genus Pseudomonas, can produce a mannose isomerase of which optimum temperature is about 55° C., higher by 15° to 20° C. as compared with the mannose isomerases known in the art. It has been also shown that the present enzyme has advantageous characteristics for industrial use, for example, the reaction is not inhibited by a substrate concentrations as high as 20 to 30%. No such mannose isomerase has been known to date. The present invention is based on such knowledge. The present inventors have prepared, and purified the mannose isomerase and further established use thereof to accomplish the present invention.

The physicochemical properties of the mannose isomerase of the present invention are described below.

(a) Enzyme Action:

This enzyme isomerizes fructose to mannose reversibly. It also acts on D-lyxose to isomerize it to D-xylulose.

Figure 1:
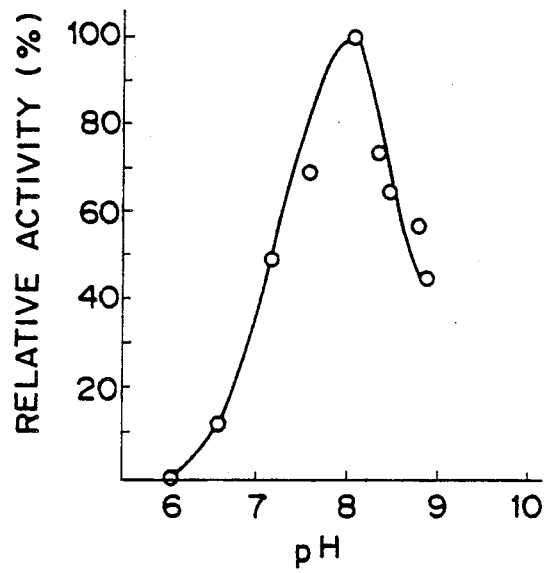
FIG. 1, FIG. 2, FIG. 3 and FIG. 4 show the optimum pH, the optimum temperature, the thermal stability and the pH stability of the mannose isomerase of the present invention, respectively.

(b) Substrate specificity:

It is active on D-mannose and D-lyxose, but not substantially on D-rhamnose, D-fucose, D-glucose, D-ribose, D-xylose, D-arabinose, L-xylose, L-arabinose, L-rhamnose, L-fucose;

(c) Active pH and optimum pH:

It is active in a pH range from about 6 to 11, but the optimum pH is about 8 (under the reaction condition of 50° C. for 30 minutes, in 0.1 M phosphate buffer). The results are shown in FIG. 1.

Figure 2:
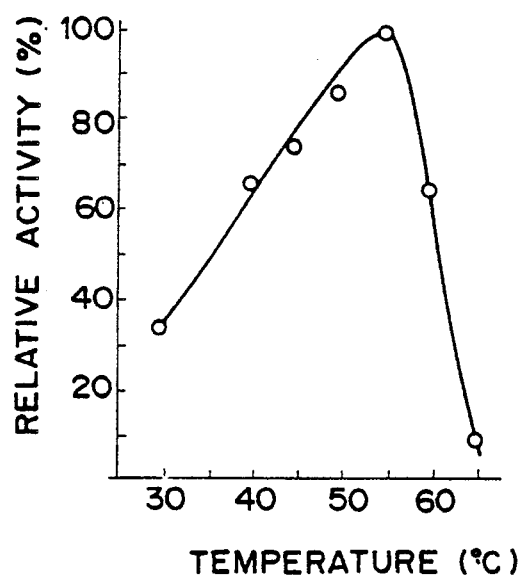

(d) Active temperature and optimum temperature:

It is active up to about 70° C., but the optimum temperature is about 55° C. under the reaction conditions of 0.1 M mannose, 0.05 M Tris buffer (pH 7.0) for 30 minutes. The results are shown in FIG. 2.

Figure 3:
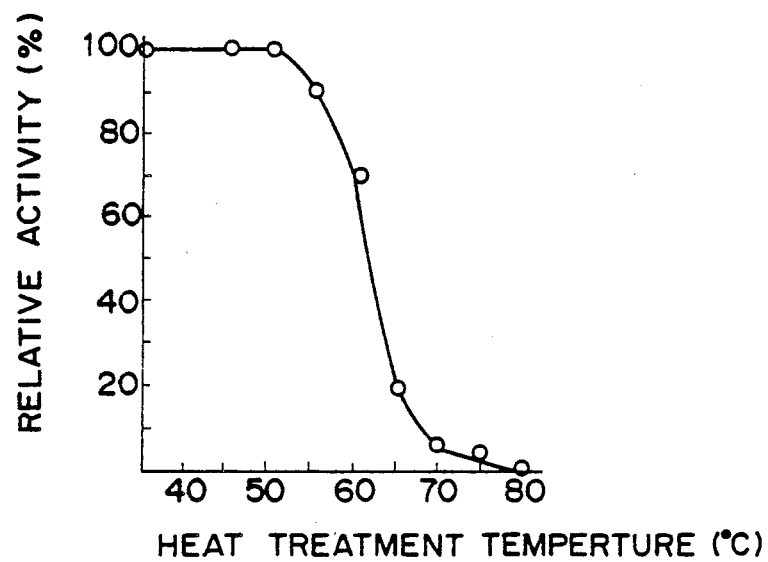

(e) Thermal stability:

The residual activities after heating treatment at 60° C. for 5, 10, 15, 20, 30 minutes in 0.05 M Tris buffer (pH 7.0) are, about 90%, 68%, 52%, 42%, 30% respectively. The results are shown in FIG. 3.

Figure 4:
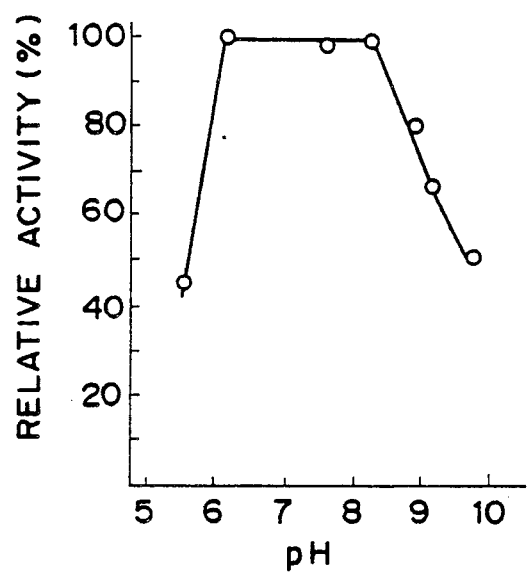

(f) pH stability:

The residual activity was measured after the enzyme was incubated in 0.1 M butter (acetate or phosphate buffer) of various pH at room temperature (25° C.) for 3 hours. As the result, it is stable in the pH range 6 to 9. The results are shown in FIG. 4.

Figure 5:
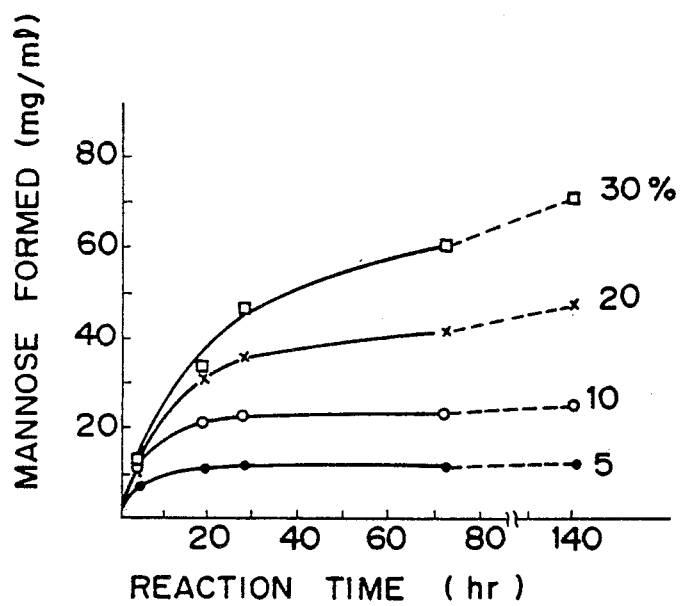
FIG. 5 shows the amount of mannose formed when the present enzyme was permitted to act on fructose of various concentrations. (- • - fructose 5%, -◯- 10%, -x- 20%, -☐- 30%).

(g) Stabilization:

The presence of calcium ions increases the thermal stability. The results are shown in FIG. 5.

(h) Inhibition:

It is strongly inhibited by $5 \times 10^{-3}$ M of $HgCl_2$, $FeSO_4$, $AgNO_3$, $AlCl_3$, p-chloromercury benzoate (pCMB), etc.

The main physicochemical properties of the enzyme of the present invention were compared with those of the enzymes derived from *Pseudomonas saccharophila* (hereinafter referred as enzyme A), from *Xanthomonas ruburilineans* (hereinafter referred as enzyme B) and *Streptomyces aerocolorigenes* (hereinafter referred as enzyme C). The results are shown in Table 1.

Enzyme activity is measured according to the method described below.

Into 0.5 ml of a 0.1 M phosphate buffer (pH 7.0) containing 0.2 M mannose dissolved therein is added a suitable amount of the enzyme, the total volume is made up with water to 1.0 ml, and the reaction mixture is incubated at 50° C. The amount of fructose formed is determined by the cysteine-carbazole method. The amount of the enzyme forming 1 micromole of fructose per one minute under this condition is defined as one unit.

TABLE 1

| Item | Enzyme of Invention | Enzyme A | Enzyme B | Enzyme C |
|---|---|---|---|---|
| Optimum pH | Around pH 8 | pH 7.5 | pH 7.8 | pH 7.7 |
| Stable pH | About 6~9 | — | — | — |
| Substrate | D-mannose D-lyxose | D-mannose (D-lyxose) (D-rlamnose) | D-mannose | D-mannose |
| Optimum temperature | About 55° C. | — | About 40° C. | About 37° C. |
| Stable temperature (Ca present) | up to around 55° C. (up to around 60° C.) | — | up to around 44° C. | — |
| Inhibitor | $HgCl_2$, $FeSO_4$ $AgNO_3$, $AlCl_3$ pCMB | $Hg^{2+}$, $Zn^{2+}$ $Ni^{2+}$, pCMB | $Cu^{2+}$, $Zn^{2+}$ $Ni^{2+}$, pCMB | $Cu^{2+}$, $Co^{2+}$ pCMB |
| Inhibition by glucose | no inhibition at 0.56 (10%) | inhibited at 45% at 0.25 (4.5%) | — | — |

The enzyme of the present invention has higher optimum temperature by about 15° to 20° C. when compared with the enzyme B and the enzyme C, and also higher the stable temperature by 10° C. or more. Thus, thermal stability of the enzyme is clearly different from the enzyme B and the enzyme C known in the art. When compared with the enzyme A derived from the bacteria of the same genus, it shows different substrate specificity, that is, the enzyme of the present invention acts on D-mannose and D-lyxose, while the enzyme A on D-mannose, D-lyxose and D-rhamnose. The enzyme of the present invention is less inhibited by glucose compared with enzyme A. Therefore it is practical to use this enzyme of excellent properties in production of mannose from the isomerized sugar which is prepared from glucose by glucose isomerase.

Further, differences can be also seen between the mannose isomerase of the present invention and the known enzymes A, B or C, in optimum pH, inhibitor and stabilizers.

In conclusion, the enzyme of the present invention is a novel mannose isomerase entirely different from the enzymes known in the art.

The microorganism producing the mannose isomerase of the present invention, Pseudomonas sp. AM-9582 or its mutant strains can be advantageously used for the present invention.

Pseudomonas sp. AM-9582 was newly discovered and isolated from soil, whose bacteriological properties are as described below. This mcroogranism has been deposited in Institute of Fermentation Research, Agency of Industrial Science & Technology as FERM-BP-3207.

(1) Morphology:

Shape and size of cells: rod of 0.6-0.8 by 1.0-2.0 µm;
Presence of pleomorphism of cells: not observed;
Motility: motile by multitrichous polar flagella;
Spore formation: not formed;
Gram staining: negative;
Acid fastness: negative:

2) Growth states in various media:

Nutrient agar plate cultivation 37° C., 48 hr: colonies are circular, 0.5 to 0.8 mm in diameter, smooth surface, convex, entire edges, yellow to yellowish brown, translucent with resin-like luster.

Nutrient agar slant cultivation: abandunt growth, grown in raised filiform, yellowish brown with metalic luster, greenish brown water-soluble pigment diffused within agar at lower part of slant;

Nutrient broth cultivation: no film formed, moderately turbid, tinted with yellow;

Litmus milk cultivation: liquefied but not coagulated.

(3) Physiological propeties:

Reduction of nitrate: negative;
Gas from nitrate: negative;
MR test: negative;
VP test: negative;
Indole formation: negative;
Hydrogen sulfide formation: negative;
Hydrolysis of starch: negative;
Utilization of citric acid: utilized in both media of Simmons and Christensen;
Pigment formation: no pigment formation in media of King A, King B;
Urease: negative;
Oxidase: negative (slight, if any);
Catalase: positive;
OF test: oxidative type;
Arginine dihydrolase: positive;
Acyl amidase: positive;
Amino acid decarboxylase (lysine, ornithine): negative:
DNase: negative;
Growth temperature no growth at 41° C. or more;
Oxygen requirement: aerobic;
Growth with sodium chloride: 0–4(%) Nacl;
Acid formation from sugars:

|  |  |
|---|---|
| Galactose | + |
| Glucose | + |
| Saccharose | + |
| Trehalose | + |
| L-arabinose | + |
| Cellobiose | + |
| Xylose | + |
| Lactose | + |
| Glucose | + |
| Mannose | + |
| Mannitol | + |
| Fructose | + |
| Salicin | + |
| Starch | − |

Decomposition of gelatin (Frazier method): positive;
TSI agar medium (acid production in slant): (acid production in butt):
SS agar medium: no growth;
NAC agar medium: no growth;
MacConkey agar medium: growth;
Triphenyltetrazolium (0.1%) agar medium: growth;
Acid formation from 10% lactose: positive;
Esculin decomposition: positive (slight);
Phenylalanine deaminase: negative;
Hydrolysis of Tween 80: positive;
Reaction of 0.1% Methylene Blue milk:
reductively liquefied;
ONPG reaction: positive;
Levan production: negative:
Mucoid colony formation: negative.

Concerning the above-mentioned bacteriological properties, reference was made to Bergey's Mannual of Systematic Bacteriology, Vol. 1 (1984), and their properties were compared. As the result, the present microorganism, a straight rod producing a yellow pigment and a water soluble pigment, having polar flagella, negative in nitrate reduction, oxidase negative, Tween 80 decomposition positive, low in sodium chloride resistance, was classified into the genus Pseudomonas. The present microorganism has physiological properties such as, levan production negative, arginine dihydrolase positive, phenylalanine deaminase negative, starch decomposition negative, acylamidase positive having microorganism width of 0.3–0.6 μm. Therefore, the present microorganism strain was judged to be a new strain and designated as Pseudomonas sp. AM-9582.

In the cultivation of the present microorganism for mannose isomerase production, conventional organic nitrogen sources used in microbial cultivation, such as meat extract, peptone, corn steep liquor, casein, may be used as well as inorganic nitrogen sources such as ammonium chloride, ammonium sulfate, etc. As the carbon source, mannose end fructose which are substrates to the mannose isomerase ere also good carbon sources, but not limited to them, various inexpensive sugars such as sucrose, isomerized sugars, glucose, maltose, lactose, galactose, sorbitol, mannitol, glycerine can be also employed, as well as starch, dextrin, etc. In addition to nitrogen and carbon sources, as the medium supplements, phosphates and various metal salts such as magnesium salts, copper salts are added.

Cultivation may be carried out at pH 5 to 9, preferably pH 6 to 8, at a temperature of 25° to 50° C., preferably 30° C., for about 2 to 4 days.

Since the mannose isomerase is an enzyme produced within microorganism cells, the cells are recovered by filtration or centrifugation after cultivation and used directly or subjected to appropriate fixing treatment before use. Alternatively the enzyme may be extracted by sonication or autolysis to be concentrated. If necessary, the enzyme may be precipitated with ammonium sulfate, acetone, methanol or ethanol, etc., dried and stored.

The present enzyme can be purified to be electrophoretically homogeneous by conventional enzyme purification methods. For example, the enzyme may be extracted from the cells by use of cetyltrimethylammonium bromide, etc., and purified by centrifugation, salting out, DEAE-Sepharose column chromatography, Sephadex G-150 column chromatography and so on.

The reaction of forming mannose from fructose by the present enzyme may be carried out at pH 6–8, at 40°–60° C. in a solution containing 10–50% of fructose. The sugar composition after the reaction was analyzed by high performance liquid chromatography.

The ratio of mannose to fructose in equilibrium was about 25 to 75.

Alternatively, the isomerization of fructose to mannose may be catalysed by the immobilized cells (source of the present isomerase) themselves. In that case, wet cells harvested from the culture are immobilized onto a cell-immobilizer such as Celite Catalyst Carriers No. R-620 (Manville. USA) and a fructose solution is applied circularly onto the packed cell-carriers.

The present invention is explained in detail by following Examples.

EXAMPLE 1

Four ml of a medium (pH 7.0) containing 1% of a fish meat extract, 1% of a carbon source listed in Table 2, 0.2% of $K_2HPO_4$ and 0.05% of $MgSO_4.7H_2O$ was put into a test tube of 18 mm in diameter, sterilized in conventional manner, inoculated with Pseudomonas sp. AM-9582 (FERMBP-3207) and incubated with to shaking at 30° C. for 2 days. After the cultivation, the culture was incubated at pH 8.0, 30° C. for 6 hours in the presence of 0.05% cetyltrimethylammonium bromide and centrifuged to extract the enzyme. Of the enzyme solution thus obtained, the mannose isomerase activity was measured. The results obtained are shown in Table 2.

TABLE 2

| Carbon source (1%) | Microorganism cell amount (660 nm) | Mannose isomerase activity (unit/ml medium) |
|---|---|---|
| Mannose | 12.6 | 0.41 |
| Fructose | 13.3 | 0.35 |
| Glucose | 9.6 | 0.26 |
| Galactose | 13.4 | 0.42 |
| Xylose | 14.6 | 0.28 |
| Sucrose | 16.7 | 0.40 |
| Maltose | 4.5 | 0.21 |
| Lactose | 6.5 | 0.20 |
| Sorbitol | 19.3 | 0.21 |
| Mannitol | 16.6 | 0.30 |
| Glyurine | 14.8 | 0.27 |

As shown in Table 2, although mannose and fructose, the substrate for the mannose isomerase, are good carbon sources, the mannose isomerase can be produced using various inexpensive sugars such as sucrose or glucose.

Further, the supernatant obtained was salted out with 60% ammonium sulfate to obtain precipitates. The precipitates were dialysed followed by DEAE Sepharose column chromatography and three cycles of gel filtration with Sephadex G150. The mannose isomerase obtained was electrophoretically homogeneous, and 290-fold purified in its specific activity.

EXAMPLE 2

In Example I, in a medium containing 1.5% of sucrose, fructose, glucose or a mixture of these as the carbon source, Pseudomonas sp. AM-9582 (FERMBP-3207) was inoculated and incubated with to shaking at 30° C. for 2 days. After the cultivation, following Example 1, the mannose isomerase activity was measured. The results are shown in Table 3.

TABLE 3

| Carbon source (1.5%) | | | Mannose isomerase activity (unit/ml) |
|---|---|---|---|
| Sucrose (%) | Glucose (%) | Fructose (%) | |
| 100 | 0 | 0 | 0.44 |
| 0 | 83 | 17 | 0.32 |
| 0 | 67 | 33 | 0.38 |
| 0 | 50 | 50 | 0.40 |
| 0 | 33 | 67 | 0.44 |
| 0 | 17 | 83 | 0.52 |
| 0 | 0 | 100 | 0.47 |

As shown in Table 3, the best results were obtained when a mixture of fructose and glucose, particularly with the composition of about 80% of fructose and about 20% of glucose, was employed as the culture carbon source.

EXAMPLE 3

In a series of media containing 2.5% of a fish meat extract, 2.5% of glucose, 1.25% of fructose, 0.15% of $K_2HPO_4$, 0.05% of $MgSO_4 \cdot H_2O$, and $CuSO_4$ in a range of $2 \times 10^{-4}$ to $8 \times 10^{-4}$ M, Pseudomonas sp. AM-9582 FERMBP-3207) was inoculated and incubated at 30° C. for 24 hours, to measure the mannose isomerase produced. The results obtained are shown in Table 4.

TABLE 4

| $CuSO_4$ (M) | Microorganism cell amount grown (660 nm) | Mannose isomerase activity (unit/ml) |
|---|---|---|
| No addition | 17.2 | 0.50 |
| $2 \times 10^{-4}$ | 16.1 | 0.48 |
| $4 \times 10^{-4}$ | 18.0 | 0.50 |
| $6 \times 10^{-4}$ | 18.1 | 0.76 |
| $8 \times 10^{-4}$ | 18.0 | 0.65 |

As is apparent from Table 4, with the addition of copper ions, the amount of the mannose isomerase produced was markedly increased.

EXAMPLE 4

The microorganism cells obtained by cultivation according to Example 3 were disrupted by 20 KC sonication for one minute, and the mannose isomerase was extracted to obtain an enzyme solution (0.42 unit/ml). Using this solution, mannose producion from fructose (substrate) was examined.

Aliquats of mannose isomerase (0.30 unit) were added into fructose solusions containing 50, 100, 200 and 300 mg fructose. The total volume was made up with water to 1.0 ml, and the reaction was carried out at pH 7.0, 45° C. Samples were taken at intervals and the amounts of the formed mannose and the residual fructose were determined by high performance liquid chromatography. The results obtained are shown in Table 5 and Table 6.

TABLE 5

| Reaction time (hrs) | Mannose amount formed (mg/ml) | | | |
|---|---|---|---|---|
| | 5% | 10% | 20% | 30% |
| 4 (h) | 7.3 | 10.5 | 10.4 | 11.4 |
| 18.5 | 11.2 | 21.3 | 32.4 | 33.0 |
| 27.5 | 12.1 | 22.3 | 36.4 | 46.5 |
| 72 | 12.2 | 23.5 | 42.0 | 60.6 |
| 140 | 13.0 | 25.7 | 48.4 | 71.1 |

As shown Table 5, the present enzyme can form mannose efficiently even under the high concentration of the substrate, yielding mannose at 24 to 26%.

EXAMPLE 5

A culture of Pseudomonas sp. AM-9582 (FERM EP-3207) was inoculated into a medium containing fish meat extract 2.5%; glucose, 2.5%, fructose, 1.25%; $K_2HPO_4$, 0.15%; $MgSO_4 \cdot 7H_2O$ 0.05%; $CuSO_4$, $6 \times 10^{-4}$ M, and incubated at 30° C. for 24 hours. Cells were harvested and 250 g of wet cells was obtained. To a solution of fructose (30%, IL), 100 g of the wet cells was added and incubated at pH7.0, 45° C. for 16 hours. The activity of the wet cells was 7 unit/g. The formed mannose was measured to be 56.3 g. The conversion ratio from fructose was 18.8%.

EXAMPLE 6

The wet cells (100 g) obtained in Example 5 was suspended in a buffer (25 mM phosphate buffer, pH7.0, 5L). The suspension was applied to a column (5×30 cm) packed with Celite Catalyst Carriers No. R-620 (Manville, USA) as a cell-immobilizer, with upward circulalization at 2.5L/hr for 7 hours. Then, the unabsorbed cells were eluted with the phosphate buffer (25 mM, pH7.0, 2.5L, 10 hours) to obtain an immobilized cell column having mannose isomerase activity.

A fructose solution (30%, pH7) was continuously applied to the column, upward, at 60 ml/hr (SV=0.1). 45° C., resulting in the continuous production of mannose of 68 mg/ml.

After the seven days' reaction, 65 mg/ml of mannose was still produced.

What is claimed is:

1. A mannose isomerase having the following physicochemical properties:
   (a) enzyme action isomerizing mannose to fructose and vice versa;
   (b) substrate specificity: active on D-mannose and D lyxose, but substantially not on D-rhamnose, D-fucose, D-glucose, D-ribose, D-xylose, D arabinose, L-xylose, L-arabinose, L-rhamnose, L-fucose;
   (c) optimum pH: about pH 8 at 50° C;
   (d) optimum temperature: about 55° C. at pH 7.0 for 30 minutes;
   (e) thermal stability: up to around 55° C., at pH 7.0 for 10 minutes;
   (f) pH stability: around pH 6 to 9 at 25° C., for 3 hours;
   (g) inhibition: enzyme activity being inhibited by mercury ions, iron ions, silver ions, aluminum ions and p-chloromercury benzoate.

2. The mannose isomerase according to claim 1, which is isolated from Pseudomonas sp. AM-9582.

* * * * *